United States Patent
Buhl et al.

(10) Patent No.: US 10,234,401 B2
(45) Date of Patent: Mar. 19, 2019

(54) METHOD OF MANUFACTURING SEMICONDUCTOR DEVICES BY USING SAMPLING PLANS

(71) Applicant: Qoniac GmbH, Dresden (DE)

(72) Inventors: Stefan Buhl, Dresden (DE); Martin Roeßiger, Erlangen (DE); Georg Erley, Dresden (DE); Boris Habets, Dresden (DE)

(73) Assignee: QONIAC GMBH, Dreseden (DE)

( * ) Notice: Subject to any disclaimer, the term of this patent is extended or adjusted under 35 U.S.C. 154(b) by 270 days.

(21) Appl. No.: 15/049,495

(22) Filed: Feb. 22, 2016

(65) Prior Publication Data

US 2017/0242425 A1    Aug. 24, 2017

(51) Int. Cl.
| | |
|---|---|
| *G01N 21/95* | (2006.01) |
| *G05B 19/418* | (2006.01) |
| *G03F 7/20* | (2006.01) |
| *H01L 21/66* | (2006.01) |

(52) U.S. Cl.
CPC ..... *G01N 21/9501* (2013.01); *G03F 7/70616* (2013.01); *G03F 7/70625* (2013.01); *G05B 19/4188* (2013.01); *G05B 19/41875* (2013.01); *H01L 22/20* (2013.01); *G05B 2219/37224* (2013.01); *G05B 2219/45031* (2013.01); *H01L 22/12* (2013.01); *Y02P 90/02* (2015.11)

(58) Field of Classification Search
CPC .................. G05B 19/4188; G05B 2219/45031
See application file for complete search history.

(56) References Cited

U.S. PATENT DOCUMENTS

| | | | |
|---|---|---|---|
| 6,442,496 B1 * | 8/2002 | Pasadyn | H01L 21/67276 257/E21.525 |
| 2008/0201117 A1 * | 8/2008 | Wong | G06F 17/5009 703/2 |
| 2009/0192743 A1 * | 7/2009 | Ikeda | G05B 19/41875 702/83 |
| 2013/0310966 A1 * | 11/2013 | MacNaughton | G03F 7/70525 700/121 |
| 2014/0354969 A1 | 12/2014 | Elings et al. | |

* cited by examiner

*Primary Examiner* — Ajay Ojha
(74) *Attorney, Agent, or Firm* — 24IP Law Group USA, PLLC; Timothy Dewitt

(57) ABSTRACT

A method of manufacturing semiconductor devices includes defining a sampling plan that contains position information about metrology sites on process wafers. A first property of the process wafers is measured to obtain measurement values at measurement points, wherein a quantity of the measurement points per process wafer is at least tenfold a quantity of the metrology sites. A sampling model that includes at least a wafer model is updated on the basis of the measurement values. The sampling plan is updated on the basis of an assessment of deviations of the measurement values from a current sampling model.

23 Claims, 11 Drawing Sheets

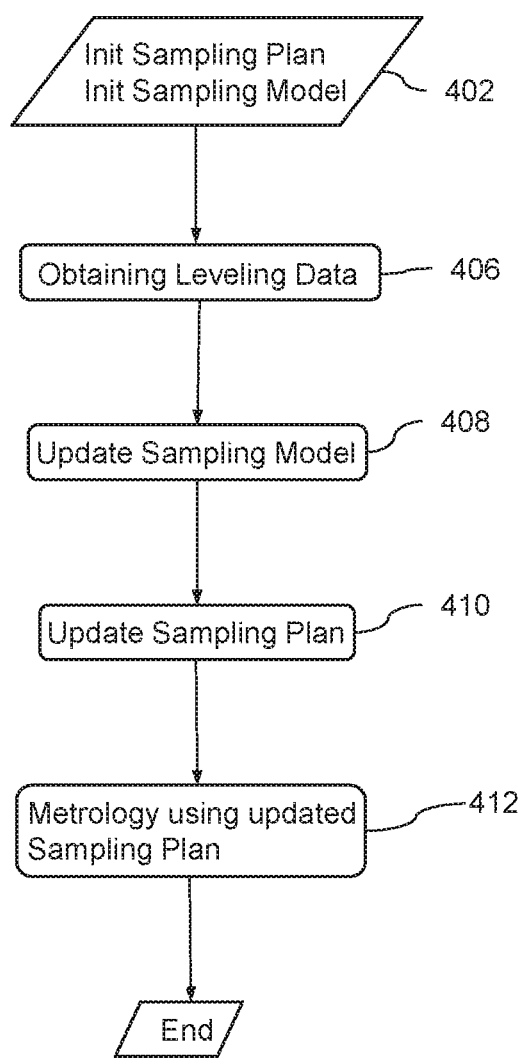

METHOD OF MANUFACTURING SEMICONDUCTOR DEVICES BY USING SAMPLING PLANS

CROSS-REFERENCE TO RELATED APPLICATIONS

None.

STATEMENT REGARDING FEDERALLY SPONSORED RESEARCH OR DEVELOPMENT

None.

BACKGROUND

Field of the Disclosure

The embodiments concern methods of manufacturing semiconductor devices using sampling plans as well as process control in semiconductor wafer processing.

Description of Related Art

In the course of manufacturing semiconductor elements, metrology tools monitor the results of process steps effective on wafers. Results of wafer metrology may be used for fault detection, for determining abnormal equipment states, for executing tool alarms, for examining the cause of faults and for classifying a process wafer as a faulty wafer or as a wafer in line with target tolerances. Feed forward control uses the results of previous inspections for adjusting process parameters of following processes. Run-to-run control automatically changes process recipe parameters for a given wafer or wafer lot on the basis of feed-back data from post-process metrology applied to a previous run. APC (advanced process control) combines aspects of fault detection, classification, feed forward control and run-to-run control. Metrology sites may include specially designed measurement targets and/or portions of a product pattern.

Wafer metrology aims at an economic trade-off between metrology costs and yield improvement. Typically, wafer metrology uses a sampling plan defining the position of a number of metrology sites on selected process wafers of a wafer lot and exclusively measures selected process wafers at the metrology sites identified in the sampling plan. The metrology sites may be within exposure fields, outside of exposure fields, e.g., in a wafer edge area, within chip areas and/or outside of the chip areas, e.g., in kerf areas of a wafer.

Sampling plans may be changed inbetween successive lots of semiconductor wafers to adjust for a changed state of the exposure and processing equipment. US 2014/0354969 A1 assigns a plurality of substrates to different sub-sampling plans.

There is a need for improving the effectiveness of sampling plans and for increasing the efficiency of the sampling plans.

SUMMARY OF THE INVENTION

According to an embodiment, a method of manufacturing semiconductor devices includes defining a sampling plan that contains position information about metrology sites on process wafers. A first property of the process wafers is measured to obtain measurement values at measurement points, wherein a quantity of the measurement points per process wafer is at least tenfold a quantity of the metrology sites. A sampling model that includes at least a wafer model is updated on the basis of the measurement values. The sampling plan is updated on the basis of an assessment of deviations of the measurement values from a current sampling model.

According to another embodiment a process control system for a semiconductor manufacturing assembly includes a sampling model module that updates a sampling plan comprising at least a wafer model on the basis of measurement values obtained from a process wafer. A sampling plan module updates a sampling plan for wafer inspection on the basis of an assessment of deviations of the measurement values from a current sampling model.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

FIG. 1B is a simplified schematic flow chart of a method of manufacturing semiconductor devices using an adaptive wafer model for adapting sampling plans according to an embodiment.

DETAILED DESCRIPTION

Figure 1A:
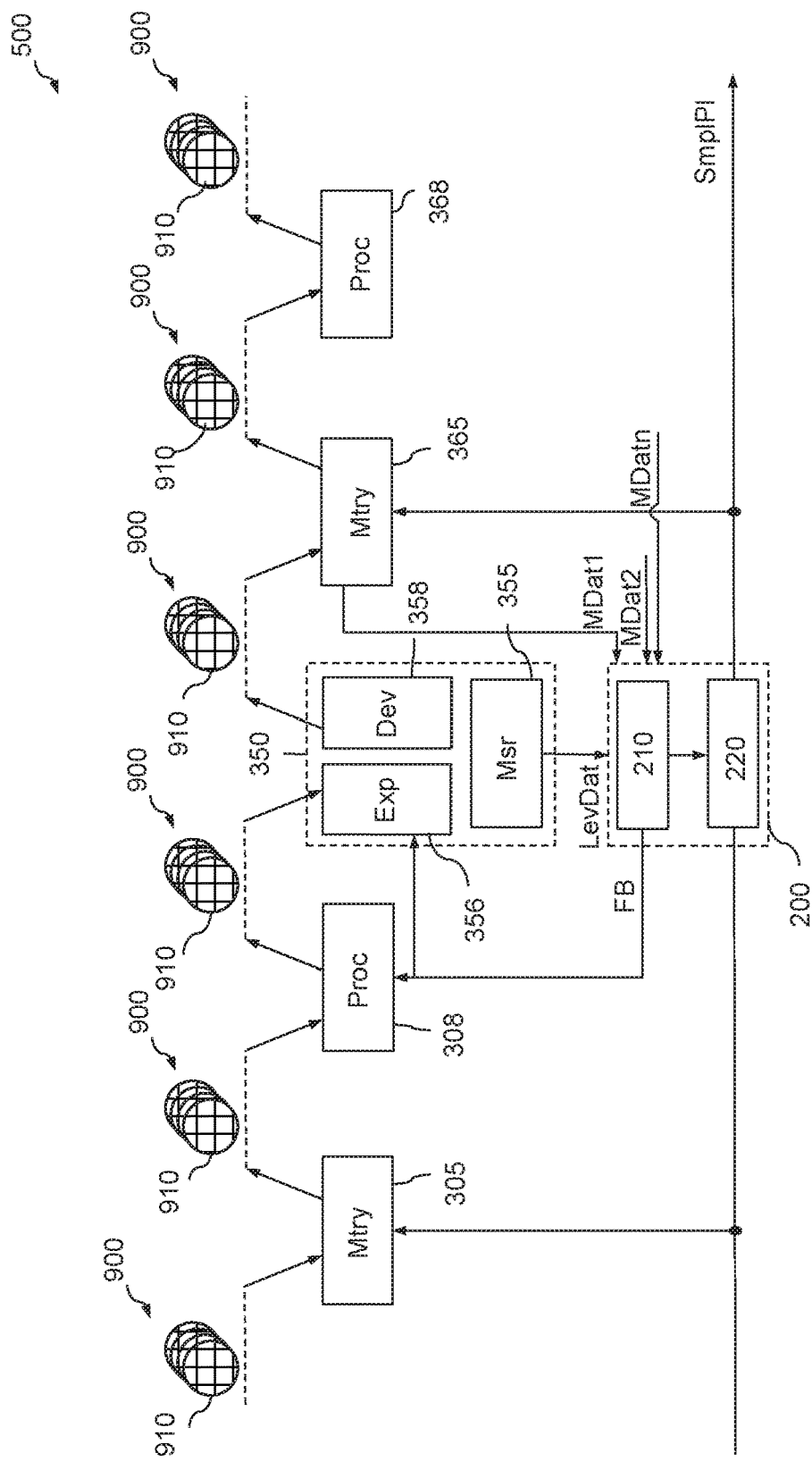
FIG. 1A is a schematic block diagram of a section of a semiconductor manufacturing assembly using an adaptive wafer model and adaptive sampling plans according to an embodiment.

In the following drawings, like reference numerals designate identical or corresponding parts throughout different views. The elements of the drawings are not necessarily to scale relative to each other. Features of the illustrated embodiments can be combined with each other to obtain further embodiments.

FIG. 1A shows a section of a semiconductor manufacturing assembly 500 for process wafers 910, which are supplied to the semiconductor manufacturing assembly 500 in wafer lots 900, wherein process wafers 910 belonging to the same wafer lot 900 are processed in the same or at least similar way in close temporal relation, e.g., partly contemporaneously and/or directly one after another. The semiconductor manufacturing assembly 500 includes a plurality of process tools 308, 350, 368 for patterning processes, deposition processes, etch processes, implantation processes and heating treatments, by way of example. Metrology tools 305, 365 inspect the process wafers 910 at a number of metrology sites distributed across and among the process wafers 910 of a wafer lot 900 and defined in a sampling plan. Between the illustrated process and metrology tools 305, 308, 350, 365, 368 the process wafers 910 may be loaded to further process and metrology tools.

The sampling plan may include wafer identification information for identifying specific process wafers 910 in a wafer lot 900 and further includes position information identifying the metrology sites on the process wafers 910 selected for inspection. The metrology sites may have circular, elliptical or rectangular shape. The size of the metrology sites depends on the measurement method. A diameter or edge length of the metrology sites may be about 100 µm for scatterometric methods and about 1 µm for measurements using electron microscopy.

The metrology tools 305, 365 inspect the process wafers 910 and obtain physical information about the concerned process wafer 910 at and around the metrology sites identified in the sampling plan. The physical information may contain geometric dimensions such as height, width and/or length of a structure on a surface of the process wafer within the measurement area, e.g., a width of a line or a vertical extension of a step or a trench, a sidewall angle of a protrusion extending from a surface of the process wafer 910, or a sidewall angle of a trench extending into a surface of the process wafer 910. Alternatively or in addition the physical information may contain information about thickness and/or composition of a topmost layer covering the process wafer 910 or about other physical properties or characteristics such as line edge roughness, line width roughness, overlay data, wafer shape, wafer deformation, defect density as well as about results of defect and electrical measurements.

A metrology tool 305 may inspect the process wafers 910 according to a current sampling plan. Then the process wafers 910 may be subjected to at least one further process in a further process tool 308 or may be directly supplied to a high-resolution metrology tool 355 or to an assembly of tools that includes a high-resolution metrology tool 355.

The high-resolution metrology tool 355 may obtain measurement values at measurement points for each process wafer 910 of a wafer lot 900. The measurement values may be or may contain levelling data, e.g., levelling data of the process wafers 910 in a state, in which the process wafer 910 is firmly pressed against a flat support base to obtain a dense height map of the concerned process wafer 910 in a chucked state, wherein the process wafer 910 may be electrostatically-chucked or vacuum-chucked at the support base. In the chucked state a global warping or bowing of the process wafer 910 is at least partly or almost completely smoothed.)

Alternatively or in addition, the measurement values may refer to other physical properties, for example height maps obtained from unchucked process wafers 910 and including information about wafer bowing and wafer warping. The measurement values represent information on significantly more measurement points than metrology sites are contained in the sampling plan, e.g., a quantity of the measurement points per wafer is at least tenfold or at least hundredfold the mean quantity of the metrology sites per wafer.

The high-resolution metrology tool 355 may be an isolated metrology tool or may be part of an assembly as illustrated in FIG. 1A. According to an embodiment the assembly is a lithography assembly 350 and the high-resolution metrology tool 355 is an optical measurement unit, e.g., a scatterometer or a laser measurement unit integrated in or data-linked with an exposure unit 356 of the lithography assembly 350. The optical measurement unit obtains levelling data from the process wafers 910 and transmits the levelling data to a controller that controls a projection tool and/or a support stage of the exposure unit 356. The controller may control the projection tool and/or the support stage to locally adapt focal position and/or exposure dose in response to local levelling data.

A developer unit 358 of the lithography assembly 350 may further process the process wafers 910. For example, after exposure by the exposure unit 356, the developer unit 358 may subject the process wafer 910 to a developing process for developing the exposed resist and to a rinsing process for selectively removing the exposed portions of the developed resist with respect to the unexposed portions or vice versa.

A process control system 200 includes a sampling model module 210 that receives the measurement values, e.g., the levelling data used by an exposure tool, and updates a sampling model for the process wafers 910.

The sampling model may include a wafer model. The wafer model is based on a model function describing a quantifiable physical property as a function of one or more position variable(s) in closed form, wherein at least some or all of the coefficients of the model function are variables and wherein the wafer model may contain absolute and/or relative boundary values for some or all of the coefficients. The wafer model may cover a complete wafer, wherein the model function may be rotationally symmetric or point-symmetric with respect to a centre point of the process wafers 910 or may show no sort of rotational symmetry. Alternatively or in addition, the wafer model may cover wafer sections, e.g., single exposure fields or groups of exposure fields. The sampling model may include a plurality of wafer models of different types, wherein each process wafer 910 may be evaluated with respect to more than one wafer model.

A specific set of coefficients for one of the model functions of the wafer model defines a wafer model instance. For description of a wafer model instance, the measurement values obtained from a collection of the process wafers 910 may be successively averaged, wherein outliers may be discarded before calculating the local average values.

A wafer model instance may be descriptive for a complete wafer area or for a wafer section, e.g., an exposure field or a group of exposure fields. For example, a wafer model instance may be obtained by fitting selected exposure fields of the same wafer or by fitting corresponding exposure fields of different process wafers 910, wherein corresponding exposure fields have the same position with respect to a wafer notch. Continuously updating a wafer model instance with values of the pertinent physical property obtained for each new process wafer assigned to the same collection gives a time response of the wafer model instance and of a process linked to the wafer model instance.

A collection of process wafers 910, may be, for example, a set of process wafers 910 subjected to equivalent processing at the same process tool such that a specific wafer model instance contains information on a specific process tool. By comparing the wafer model instances of different collections of process wafers 910 subjected to equivalent processes at different process tools, specific position-dependent process or process tool signatures may be extracted from the wafer model instances. A further embodiment of a collection of process wafers 910 may be the wafers of the same wafer lot such that the temporal variation of a physical characteristic across a wafer lot can be observed.

A trend in a wafer model instance or a process tool signature may be observed and analysed. An assessment of trends in the wafer model instances and/or process tool signatures may result in determining control parameters adapted for at least partly compensating a trend occurring in a specific process or process tool. The control parameters may either be transmitted as feedback signals for the observed processes or process tools and/or for other processes or process tools the process wafers 910 are subjected to or loaded at before being processed at the lithography assembly 350, and/or as feed forward signals for process tools the process wafers 910 reach after leaving the lithography assembly 350.

The sampling model may further include a threshold model that may include one or more position-independent threshold values. According to another embodiment, the threshold model may contain one or more position-dependent threshold functions, wherein the threshold functions may be rotationally symmetric or point-symmetric with respect to a centre point of the process wafers 910 or may show no sort of rotational symmetry. According to another embodiment the threshold model compares, for each target chip area or for each target exposure field a comparison area that includes one, two, four or more chip areas neighbouring the target chip area or that includes one, two, four or more exposure fields neighbouring the target exposure field. The threshold model may be static or adaptive.

The coefficients of the wafer model instances as well as the coefficients of the threshold model may be initialized with values obtained from a first one of the process wafers 910, with target values, or with values obtained from a sample specimen. The sampling model module 210 may update the wafer model instances and, if applicable, the coefficients of the threshold models with each process wafer 910 inspected at the high-resolution metrology tool 355.

Using information derived from the updated sampling model, e.g., by identifying both regions on the process wafers 910 with high information content about tool signatures and regions with low information content about the tool signatures, and/or by comparing a deviation of the measurement values of the current process wafer 910 from the updated wafer model instances with thresholds defined in the threshold model, a sampling plan module 220 may modify the sampling plan at least for the concerned process wafer 910 or the concerned wafer lot 900 in a way that a high number of sampling points is defined in regions of high interest and only a minimum number of sampling points is defined in regions of low interest.

A further metrology tool 365 may use the updated sampling plan for the concerned process wafer 910 or for one or more following process wafers 910 of the current wafer lot 900 to obtain more reliable process information, e.g., about the resist pattern formed in the lithography assembly 350. Data obtained from the updated wafer model may also be fed back to a process tool of the lithography assembly 350 or to process tools 308 effective on the process wafers 910 before inspection at the high-resolution metrology tool 355 in order to improve run-to-run control.

For example, the process tool 308 may be a deposition tool for depositing a layer onto a surface of the process wafer 910, wherein the deposited layer may be patterned by using a resist deposited, exposed and developed in the lithography assembly 350. Metrology data from the metrology tool 365 and from further metrology tools may also update the sampling model and the sampling plan through suitable data links to the process control system 200.

By continuously updating the wafer model instances for different wafer collections and by adapting the sampling plan to the wafer model instances, the metrology sites identified in the sampling plan deliver more significant information for reliably characterizing process wafer properties at low effort. By using the continuously adapted wafer models instances and sampling plans, process control can be significantly improved.

Each of the sampling model module 210 and the sampling plan module 220 may be realized in hardware, software, or a combination thereof. For example, at least one of the sampling model module 210 and the sampling plan module 220 may be or may include a processing unit that predominantly performs computer operations for carrying out the described functionality. According to other embodiments, at least one of the sampling model module 210 and the sampling plan module 220 is a computer capable of performing instructions stored on a non-transitory computer-readable medium.

FIG. 1B illustrates a flow chart of an embodiment of the method applied through the semiconductor manufacturing assembly 500 of FIG. 1A. A sampling plan as well as coefficients of a sampling model may be initialized according to previously obtained knowledge, e.g., by values of experience, by using a sample specimen, by target values or by parameters obtained from a first process wafer (402). One or more process wafers are subjected to processes such as heating treatments, layer formation processes, patterning processes, etch processes, grinding processes or implants. Metrology tools may inspect the process wafers at metrology sites defined in the sampling plan, e.g., for process control. Measurement values for measurement points may be obtained at a high-resolution metrology tool (406). For example, levelling data of chucked process wafers may be obtained in an exposure tool that uses levelling data for locally adjusting exposure dose and/or focal position in response to local height data. Alternatively or in addition, height maps of unchucked process wafers may be obtained. The measurement values, e.g., the levelling data, are used to update the sampling model, for example, by adapting coefficients of wafer model instances as well as coefficients of one or more threshold models, wherein fitting algorithms for coefficients of, e.g., Legendre polynomials may be used (408).

The sampling plan is updated on the basis of the updated sampling model (410). For example, the updated sampling model may show that some of the metrology sites of the initial sampling plan are in regions that contain only few information about process tool signatures such that the updated sampling plan omits concerned metrology sites without significant loss of information about the process tool signatures. Alternatively or in addition, the sampling model may show that the initial sampling plan contains only a low number of metrology sites in regions from which significant information about the process tool signatures can be obtained, such that the updated sampling plan adds metrology sites in the concerned wafer regions. According to another embodiment the sampling plan may include critical areas on the process wafers closely within or outside of an admissible tolerance range. Further metrology tools for inspecting the process wafers, run-to-run control and/or feedback loops may use the updated sampling plan and/or the updated sampling model (412). Further process steps such as heating treatments, layer formation and patterning processes may precede or may follow the inspection at the further metrology tools.

Figure 2A:
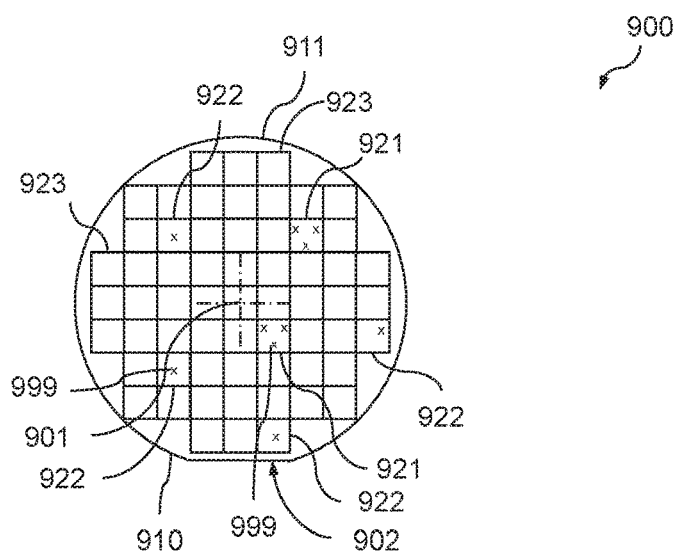
FIGS. 2A-2C illustrate a sampling plan effective on a wafer lot for discussing background helpful for an understanding of the embodiments.
Figure 2B:
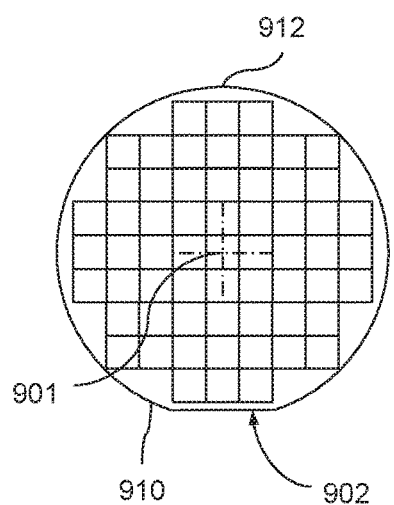
Figure 2C:
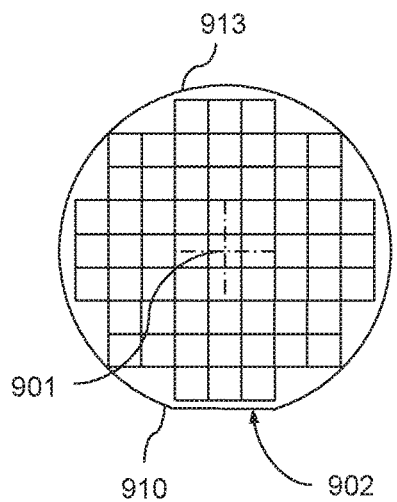

FIGS. 2A-2C illustrate a sampling plan for a wafer lot 900 that includes a batch of, e.g., 25 process wafers 911, 912, 913, . . . . The sampling plan may identify a plurality of metrology sites 999 in one or more first exposure fields 921 on a subset of the process wafers 911, 912, 913, of the wafer lot 900, for example, on a first process wafer 911, e.g., by their coordinate values, which may be Cartesian coordinate values, polar coordinate values defined with respect to a centre point 901 and a wafer notch 902, by way of example. For example, the metrology sites 999 may be defined by a combination of an index identifying an exposure field and of Cartesian coordinate values referring to the centre of the respective exposure field.

Further second exposure fields 922 may include further metrology sites 999, wherein relative positions of the metrology sites 999 within the second exposure fields 922 may correspond to each other, and wherein the quantity of metrology sites 999 per second exposure field 922 may vary across the process wafer 910. Other exposure fields 923 may be devoid of any metrology sites 999. According to other embodiments, the metrology sites 999 may be assigned to different partial sampling plans defined for different ones of the process wafers 911, 912, 913, . . . . The total number of metrology sites for a wafer lot 900 with process wafers 911, 912, 913, . . . with a diameter of 200 mm or more may be between about 10 and about 10 000.

Figure 3A:
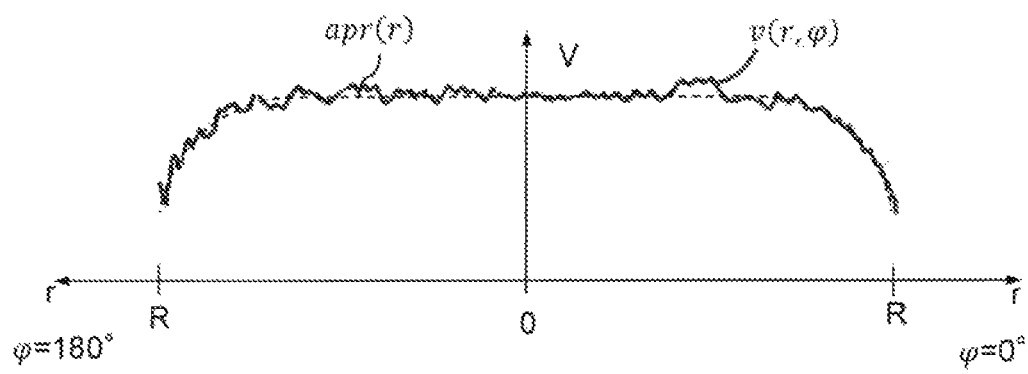
FIG. 3A is a schematic diagram plotting measurement values along a cross-section of a process wafer for illustrating the mode of operation of a sampling model module according to an embodiment.
Figure 3B:
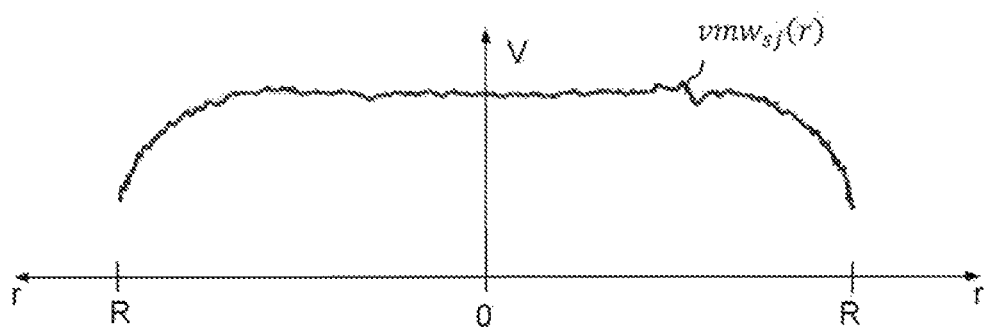
FIG. 3B is a schematic diagram plotting a wafer model instance for illustrating a mode of operation of a sampling model module according to an embodiment.
Figure 3C:
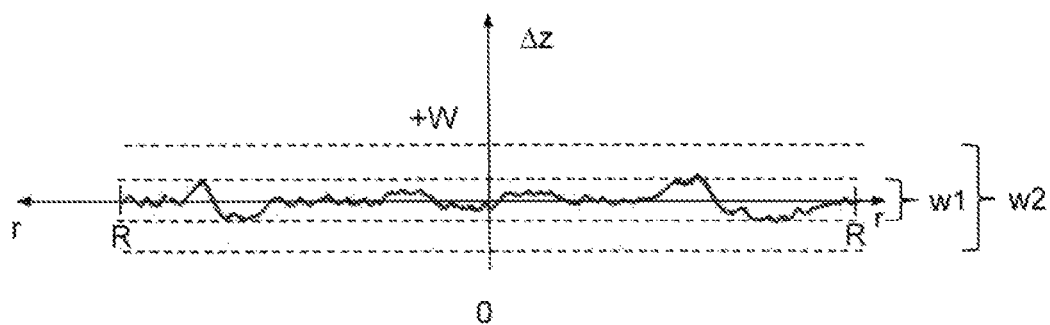
FIG. 3C is a schematic diagram plotting a deviation of measurement values obtained from a process wafer from the wafer model instance for illustrating effects of the embodiments.

FIGS. 3A to 3C illustrate the update of a sampling model that includes a wafer model instance and a threshold function.

In FIG. 3A the continuous line shows measurement values v(r,φ) obtained from a process wafer with a radius R in a high-resolution metrology tool at positions defined by a distance r to a centre point and an azimuthal angle φ defined with respect to a wafer notch. The measurement values v(r,φ) may represent levelling data with or without wafer bow, CD-data or any other physical characteristic. The dashed line shows a point symmetric approximation function apr(r) that may approximate the distribution of the measurement values v(r,φ) in closed form, e.g., by using Legendre polynomials. Equation (1) may give the approximation function apr(r) for the j-th process wafer:

$$\mathrm{apr}_j(r) = \Sigma_{i=0}^m a_{i,j} r^i \qquad (1)$$

For example, in case m is equal 0 and the measurement values v(r,φ) are levelling data, $a_{0,j}$ represents a mean height of the j-th process wafer. The sampling model module may approximate the measurement values v(r,φ) by minimizing an error function, e.g., an error function ε(r,φ) as defined in equation (2):

$$\varepsilon(r,\varphi) = |v(r,\varphi) - \mathrm{apr}(r)| \qquad (2)$$

Then the sampling model module may update the coefficients of one or more wafer model instances, e.g., the coefficients $b_{s,i,j}$ of a wafer model instance $vmw_{s,j}(r)$ for a collection s of j process wafers. By way of example, the collection s may include all process wafers exposed at the same exposure position, e.g., on the same chuck in a lithography assembly including two or more chucks. According to another embodiment, the collection s may include some or all process wafers of the same wafer lot. Calculation of the coefficients $b_{s,i,j}$ may be based on equation (3):

$$vmw_{s,j}(r) = \Sigma_{i=0}^m b_{s,i,j} r^i \qquad (3)$$

The coefficients $b_{s,i,j}$ may be obtained, for example, by equally weighting the process wafers 1 to j of collection s as indicated in equation (4). Other embodiments may provide varying weights depending on the values of the coefficients $a_{0,j}$ and/or depending on at least one of the indices i and j.

$$b_{s,i,j} = \frac{(j-1) \cdot b_{i,j-1} + a_{i,j}}{j} \qquad (4)$$

FIG. 3B illustrates the updated model function $vmw_{s,j}(r)$, which may be considered as a mean function of the previous approximations $apr_k$ with k=1 to j for process wafers of the same collection s. In the same way the coefficients $b_{t,i,j}$ for the process wafers of another collection t including all process wafers exposed at a further chuck in the lithography assembly may be obtained.

The threshold model may define a first threshold window for identifying first regions (sweet spots) of the process wafer with low deviations from the current wafer model instance $vmw_{s,j}(r)$ of a collection s. In addition or alternatively, the threshold model may define a second threshold window for identifying second regions (hot spots) with comparatively large deviations from the current wafer model instance $vmw_{s,j}(r)$. Each of the first and second threshold windows may be position-independent or position-dependent. For example, at least one of the first and second threshold windows is defined by a non-constant point symmetric function.

The sampling model module may update at least one of the first and second threshold windows w1, w2 by considering the measurement values, e.g., the levelling data. For example, if the measurement values indicate that fluctuations of wafer height are generally lower than a current threshold model indicates, the threshold windows may be narrowed at least for a subrange of the wafer radius r. If the measurement values indicate that the wafer height varies to a high degree with respect to a distance to a centre point, a position-dependent threshold window may be increased accordingly.

FIG. 3C shows a position-independent first threshold window w1 and a position-independent second threshold window w2 as well as a position-dependent deviation $\Delta z(r)$ of the current process wafer from the updated wafer model defined by the current wafer model instance $vmw_{ij}(r)$ of a collection s.

The sampling plan module may compare deviations $\Delta z(r)$ at and around the metrology sites of the first sampling plan with the threshold windows w1, w2 and may skip such metrology sites from the sampling plan that transgress the second threshold window w2. Alternatively or in addition, the sampling plan module may define new metrology sites in wafer regions, in which the process wafer does not transgress the first threshold window w1 defined in the updated sampling model. Alternatively or in addition, new metrology sites may be defined in wafer regions where the deviation has absolute or relative maxima to obtain information about hot spots.)

Alternatively or in addition, if the deviation $\Delta z(r)$ exceeds the second or a third threshold window, the process control system may mark the concerned process wafer for discarding or rework.

Another embodiment uses, for each collection of process wafers, a model function $vmw_j(r,\varphi)$ defined by at least two Zernike polynomials selected from $Z_n{}^m(r,\varphi)$ and $Z_n{}^{-m}(r,\varphi)$ as defined in equations (5a) and (5b), wherein m and n are non-negative integers:

$$Z_n{}^m(r,\varphi)=R_n{}^m(r)\cos(m\varphi) \quad (5a)$$

$$Z_n{}^{-m}(r,\varphi)=R_n{}^m(r)\sin(m\varphi) \quad (5b)$$

In equations (5a) and (5b) $\varphi$ is the azimuthal angle defined, e.g., with respect to a wafer notch, r is the distance to the centre point normalized to the wafer radius and $R_n{}^m$ are the radial polynomials as defined in equations (6a) and (6b):

$$R_n^m(r) = \sum_{k=0}^{\frac{n-m}{2}} \frac{(1)^k(n-k)!}{K!\left(\frac{n+m}{2}-k\right)!\left(\frac{n-m}{2}-k\right)!} r^{n-2k} \quad (6a)$$

for $|n-m|\bmod 2 = 0$ $$R_n^m = 0 \text{ for } |n-m|\bmod 2 = 1 \quad (6b)$$

Other than polynomials $a_i$ of equation (1), the Zernike polynomials allow an angle-dependent adaptation of the wafer model instances as well as for a threshold function such that the wafer model instances may include information on any process bias or on any systematic error resulting in a tip or tilt of the value of a physical property of the wafer along two orthogonal axes. The Zernike polynomials also allow an angle-dependent adaptation of the threshold functions to such type of process variation.

The coefficients, e.g., the radial polynomials of the Zernike polynomials descriptive for a current process wafer may be obtained by minimizing an error function as described in equation (7):

$$\varepsilon(r,\varphi)=|v(r,\varphi)-f(R_n{}^m(r)\cos(m\cdot\varphi),R_n{}^m(r)\sin(n\cdot\omega))| \quad (7)$$

Then the sampling model module may update the coefficients descriptive for a wafer model instance by equated mean values similar to equation (4) above.

A wafer model instance $vmw_{sj}(r,\varphi)$ for a collection s of process wafers may contain at least some of the Zernike polynomials $Z_1{}^1$, $Z_1{}^{-1}$, $Z_1{}^{-2}$, $Z_2{}^2$, $Z_3{}^{-1}$, $Z_3{}^1$, and $Z_4{}^0$. According to an embodiment the wafer model instance $vmw_{sj}(r,\varphi)$ contains at least one Zernike polynomial centred to the centre point of the wafer model. According to a further embodiment the wafer model instance $vmw_{sj}(r,\varphi)$ contains at least two Zernike polynomials that indicate dependency on the azimuth angle $\phi$. According to another embodiment the wafer model instance $vmw_{sj}(r,\varphi)$ contains at least the Zernike polynomials $Z_1{}^1$, $Z_1{}^{-1}$, $Z_2{}^0$, and $Z_4{}^0$.

Some of the radial polynomials may directly point to typical process-induced variations of a physical characteristic of the process wafers.

The sampling plan unit may follow different strategies for updating the sampling plan cumulatively. For example, the sampling plan unit may identify, separately for each collection of process wafers, wafer regions of high interest, e.g., in view of a signature of a specific process and wafer regions of low interest in view of the concerned signature. The sampling plan unit may identify the wafer regions of high interest by comparing a current process wafer with a current sampling model, wherein the current sampling model is based on the process wafers of a certain collection up to the current process wafer. The current sampling model may include or exclude the current process wafer.

Wafer regions of high interest may be regions in which a signature of a specific process predominantly becomes evident, is subject to frequent and/or large changes, or where main polynomials have extrema or inflection points. Wafer regions of low interest may be regions in which no specific signature is evident, or in which the specific signature is well predictable and/or stable or which are distant from extrema or inflection points of main polynomials.

According to an embodiment, in case a wafer model instance indicates that a gradient of a physical characteristics shows steep and shallow sections, the regions of the process wafer where the gradient is steep may be of higher interest than the regions where the gradient is flat.

According to another embodiment, a first region in which a physical characteristic of a current process wafer deviates to a higher degree from the current wafer model instance than in a second region, the first region may be a region of high interest and the second region a region of low interest. The current wafer model instance may include information on all preceding process wafers of the same collection including or excluding the current process wafer. In addition, regions of high variance of the physical characteristic among the process wafers assessed for the current wafer model instance may be considered for determining the regions of high and low interest.

According to a further embodiment, the sampling plan unit may skip, from the original sampling plan, at least some of the metrology sites in the regions of low interest, wherein the sampling plan unit may provide a minimum density of measurement sites in the regions of low interest for process stability. Alternatively or in addition, the sampling plan unit may add, to the original sampling plan, metrology sites in the regions of high interest and/or metrology sites close to a boundary between the regions of high and low interest to monitor the validity of the boundary.

Figure 4A:
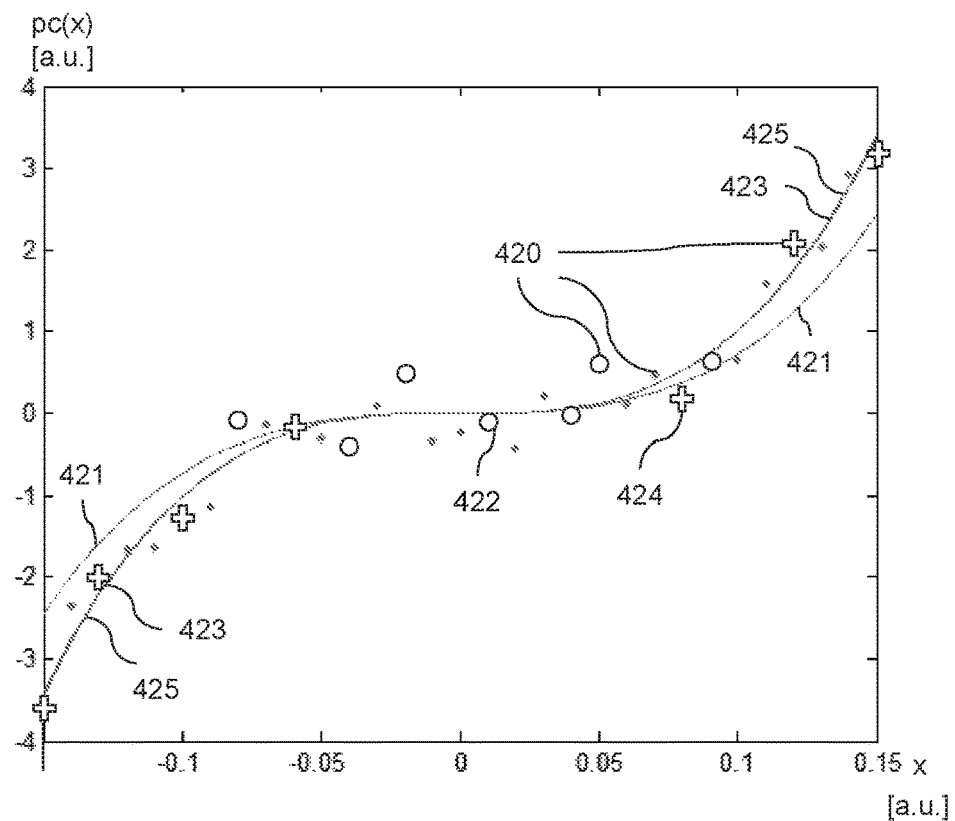
FIG. 4A is a schematic diagram visualizing an update of sampling points on the basis of measurement values for illustrating effects of the embodiments.

FIG. 4A schematically illustrates the selection of sampling points for a simplified example. The wafer model may refer to a wafer and describes a variation of a physical characteristic pc as a function of a distance x to a center point at x=0 along a straight line across the process wafer. Measurement values 420 of the physical characteristic pc are obtained in arbitrary units for equidistant measurement sites at a distance of 0.01 arbitrary length units. A first line 421 shows an approximation of the physical characteristic pc on the basis of seven of the measurement values 420 highlighted by circles 422. A second line 423 shows an approximation of the physical characteristic pc on the basis of seven other measurement values 420 highlighted by crosses 424. The second line 423 nearly perfectly approximates the optimum approximation 425 and indicates that an approximation on the basis of a low number of metrology sites selected according to one of the above discussed approaches can be sufficient for assessing the physical characteristic pc(x) with high precision. The metrology sites with the measurement values indicated by the crosses 424 may be used in an updated sampling plan.)

Figure 4B:
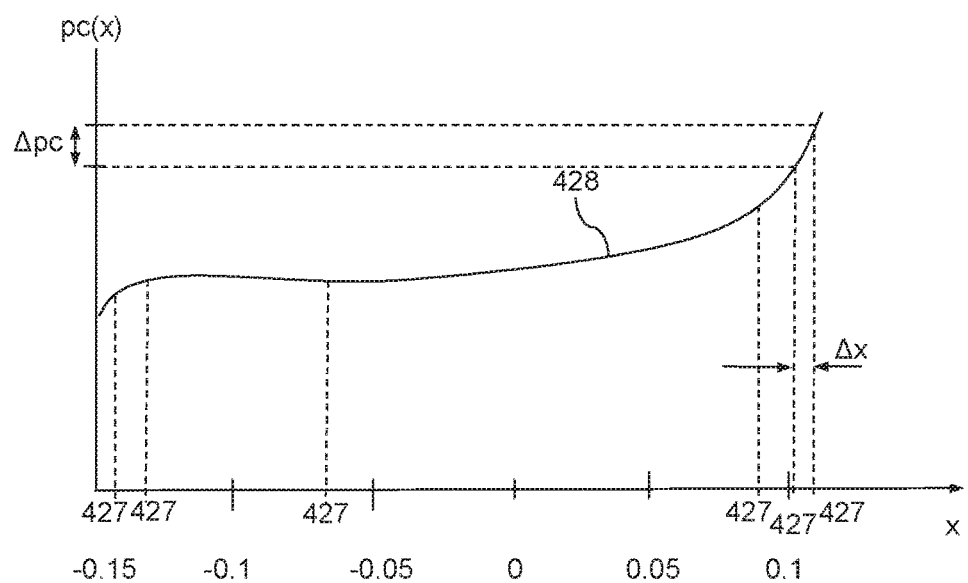
FIG. 4B is a schematic diagram illustrating the identification of regions of high interest according to an embodiment based on an assessment of a gradient of a position-dependent physical characteristic.

According to the embodiment of FIG. 4B the density of the metrology sites at positions 427 along a wafer cross-section or along an exposure field cross-section is the higher the steeper a gradient $\Delta pc/\Delta x$ of the physical characteristic pc(x) 428 described by the current wafer model instance along the wafer cross-section or exposure field cross-section is.

Alternatively or in addition, the sampling plan unit may check the degree of deviation of selected ones of the radial polynomials from a target value across the process wafer, e.g., by using individual threshold windows as described above and may replace such metrology sites, to which the model does not well fit, with metrology sites for which the current process wafer shows more agreement with the corresponding radial polynomials of the wafer model.

FIGS. 5A to 5G refer to the modification of sampling plans on the basis of updated sampling models. On the process wafers 910 on the left hand side some of the measuring sites 991 of original sampling plans are marked. On the process wafers 910 on the right hand side some of the measuring sites 991, 992 of updated sampling plans are marked.

Figure 5A:
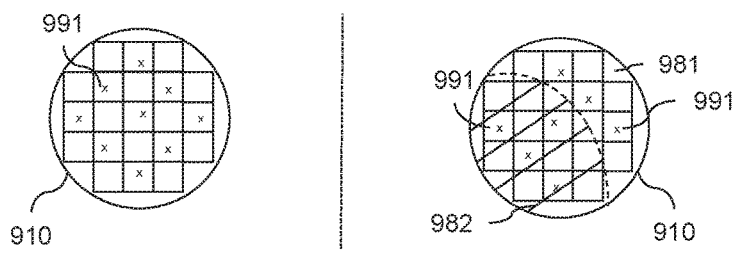
FIG. 5A is a schematic plan view of process wafers for illustrating a modification of a sampling plan according to an embodiment, wherein the modification concerns the deletion of metrology sites in wafer regions of low interest.)

In FIG. 5A the sampling model shows that some original metrology sites 991 defined by an original sampling plan are in a region of low interest 982. In the updated sampling plan some of the original metrology sites 991 in the region of low interest 982 may be deleted. The updated sampling plan may further include metrology sites 991 of the original sampling plan in a region of high interest 981.

Figure 5B:
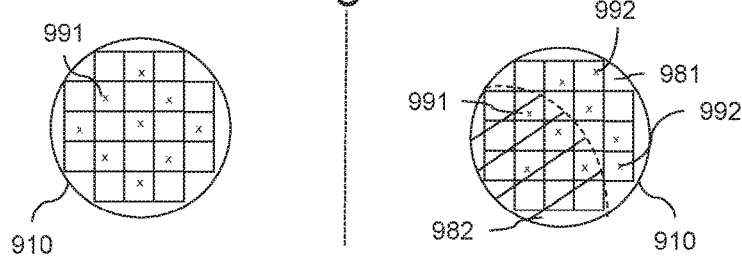
FIG. 5B is a schematic plan view of process wafers for illustrating a modification of a sampling plan according to an embodiment, wherein the modification concerns the addition of metrology sites in wafer regions of high interest.

In FIG. 5B the sampling model shows that additional metrology sites 992 in a region of high interest 981 may deliver significant information as regards a process or process tool signature. The updated sampling plan may include additional metrology sites 992 within the region of high interest 981. The original metrology sites 991 in the region of low interest 982 may be maintained in the updated sampling plan, or, as illustrated, some of them may be removed from the updated sampling plan.

Figure 5C:
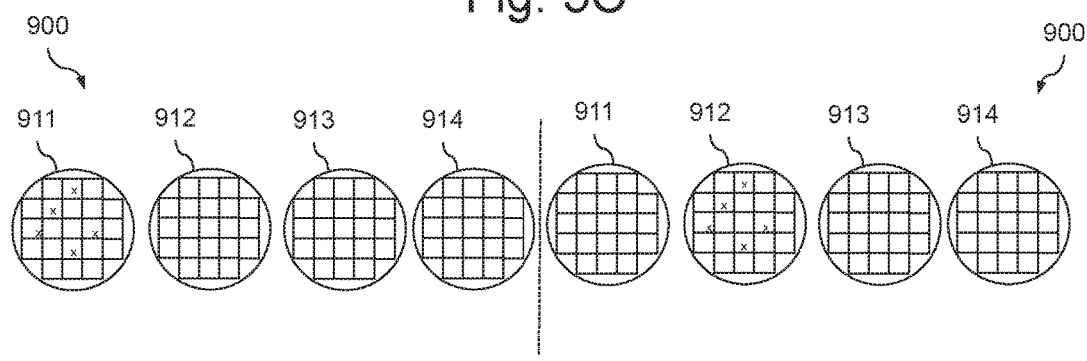
FIG. 5C is a schematic plan view of surfaces of process wafers for illustrating a modification of sampling plans according to a further embodiment, wherein the modification concerns the selection of process wafers.

In FIG. 5C the sampling model may point to the fact that a first process wafer 911 initially selected by the sampling plan is of less interest than a second process wafer 912. The updated sampling plan identifies the second process wafer 912 of the concerned wafer lot 900 for further process control metrology instead of the first process wafer 911.

Figure 5D:
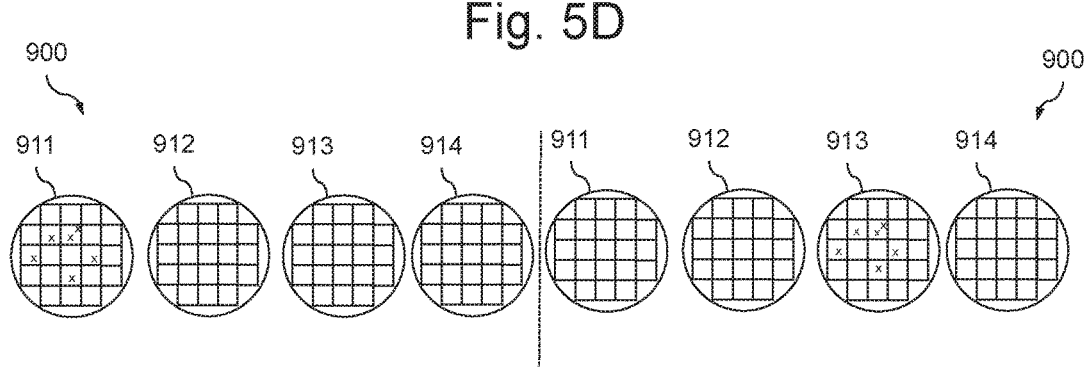
FIG. 5D is a schematic plan view of surfaces of process wafers for illustrating a modification of sampling plans according to a further embodiment, wherein the modification concerns the selection of process wafers within the same collection of process wafers.

FIG. 5D refers to an embodiment with every other process wafer belonging to the same collection, e.g., to a collection of process wafers 910 exposed on the same chuck in the same lithography assembly. Then the updated sampling plan may identify the third process wafer 913 of the wafer lot 900 for further process control metrology instead of the first process wafer 911.

Figure 5E:
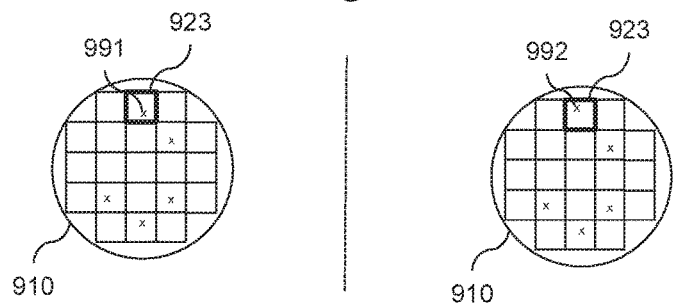
FIG. 5E is a schematic plan view of process wafers for illustrating a modification of a sampling plan according to an embodiment, wherein the modification concerns the selection of metrology sites within an exposure field.

In FIG. 5E the sampling model shows that an original metrology site 991 is in a region of low interest in one of the exposure fields 923. In the updated sampling plan the original metrology site 991 may be replaced with a new metrology site 992 in a region of high interest within the same exposure field 923.

Figure 5F:
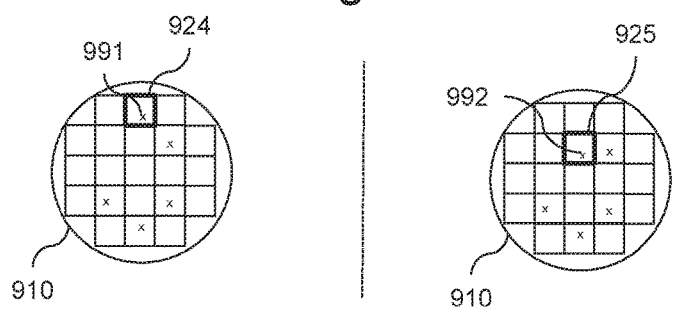
FIG. 5F is a schematic plan view of process wafers for illustrating a modification of sampling plans according to another embodiment, wherein the modification concerns the selection of exposure fields.

In FIG. 5F the updated sampling model may point to the fact that the initially selected exposure field 924 for wafer metrology is in a wafer region of low interest. The updated sampling plan may replace the original metrology sites 991 in the originally selected exposure field 924 with the new metrology sites 992 in another exposure field 925 in a wafer region of high interest, wherein the relative positions of the new metrology sites 992 within the exposure field 925 may correspond to the relative positions of the original metrology sites 991 in the original exposure field 924.

Figure 5G:
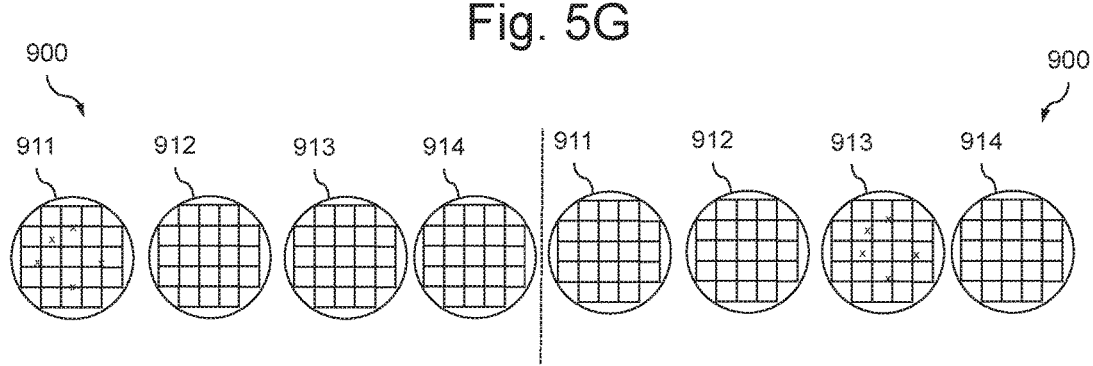
FIG. 5G is a schematic plan view of surfaces of process wafers for illustrating a modification of sampling plans according to a further embodiment concerning a combination of FIGS. 5D, 5E and 5F.

FIG. 5G combines the modifications illustrated in FIGS. 5D to 5F.

Further embodiments use further data obtained from process wafers 910 to further improve the wafer model instances. The further data may include topology data, for example information about transitions between active chip areas and peripheral chip areas, and/or between chip areas and kerf areas, where typically layer configuration and/or layer thickness may significantly change. In addition, the process control system may use data, e.g., design data descriptive for layout details that may locally influence layer thickness, data descriptive for wafer bowing and dynamic data, e.g., tracing data obtained during or after an exposure process for improving the wafer model. Further data referring to height data may be additively or substractively superimposed to such wafer model instances that basically describe height maps.

Figure 6:
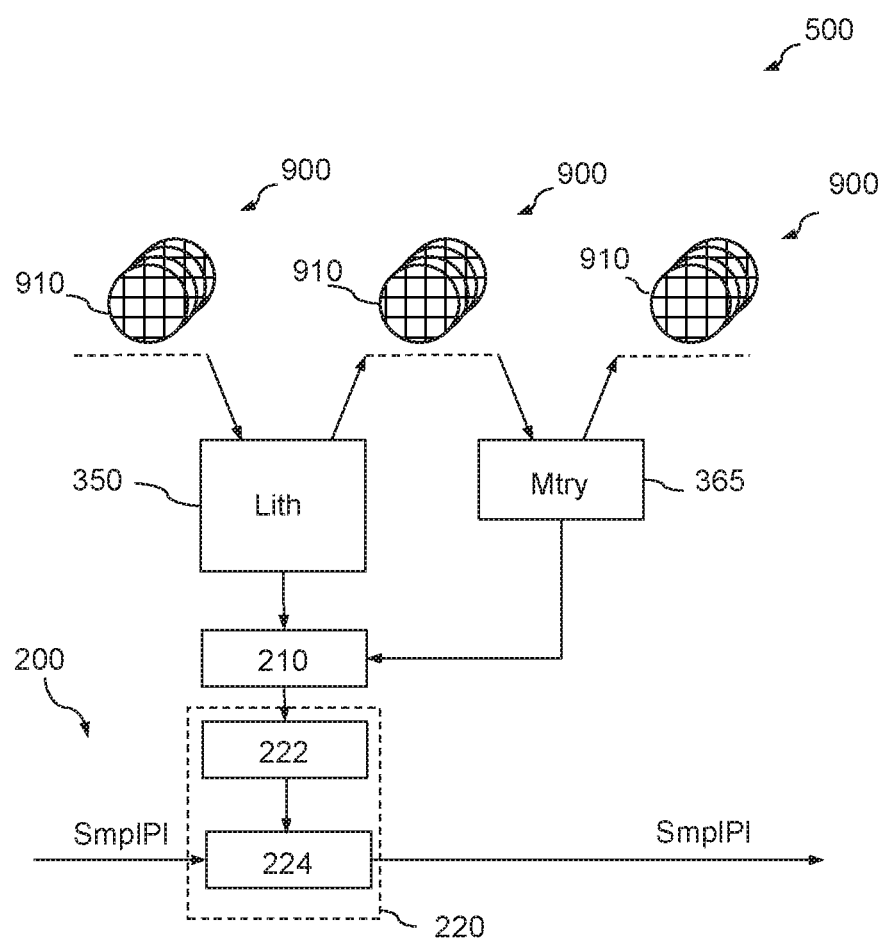
FIG. 6 is a schematic block diagram of a section of a semiconductor manufacturing assembly using an adaptive wafer model according to an embodiment concerning a modification of the wafer model on the basis of data obtained at a further metrology tool.

In FIG. 6 a data link connects a metrology tool 365, which may obtain additional data from, e.g., electrical measurements, capacitive measurements and/or optical measurements, with the sampling model module 210 of a semiconductor manufacturing assembly 500. The additional data may contain information about the accuracy of the wafer model instances. The sampling model module 210 may use the additional data obtained from the metrology tool 365 to verify and, if applicable, to adjust coefficients of the wafer model instances derived from levelling data available from a lithography assembly 350.

The sampling plan module 220 may include an evaluation module 222 that may use an adaptive threshold function or a multi-field comparison to identify regions on the process wafers 910 which are suitable for being used for compensating drifting tool or process parameters. An assignment module 224 may update a sampling plan by replacing metrology sites in wafer regions of low interest with metrology sites in wafer regions of high interest.

Figure 7:
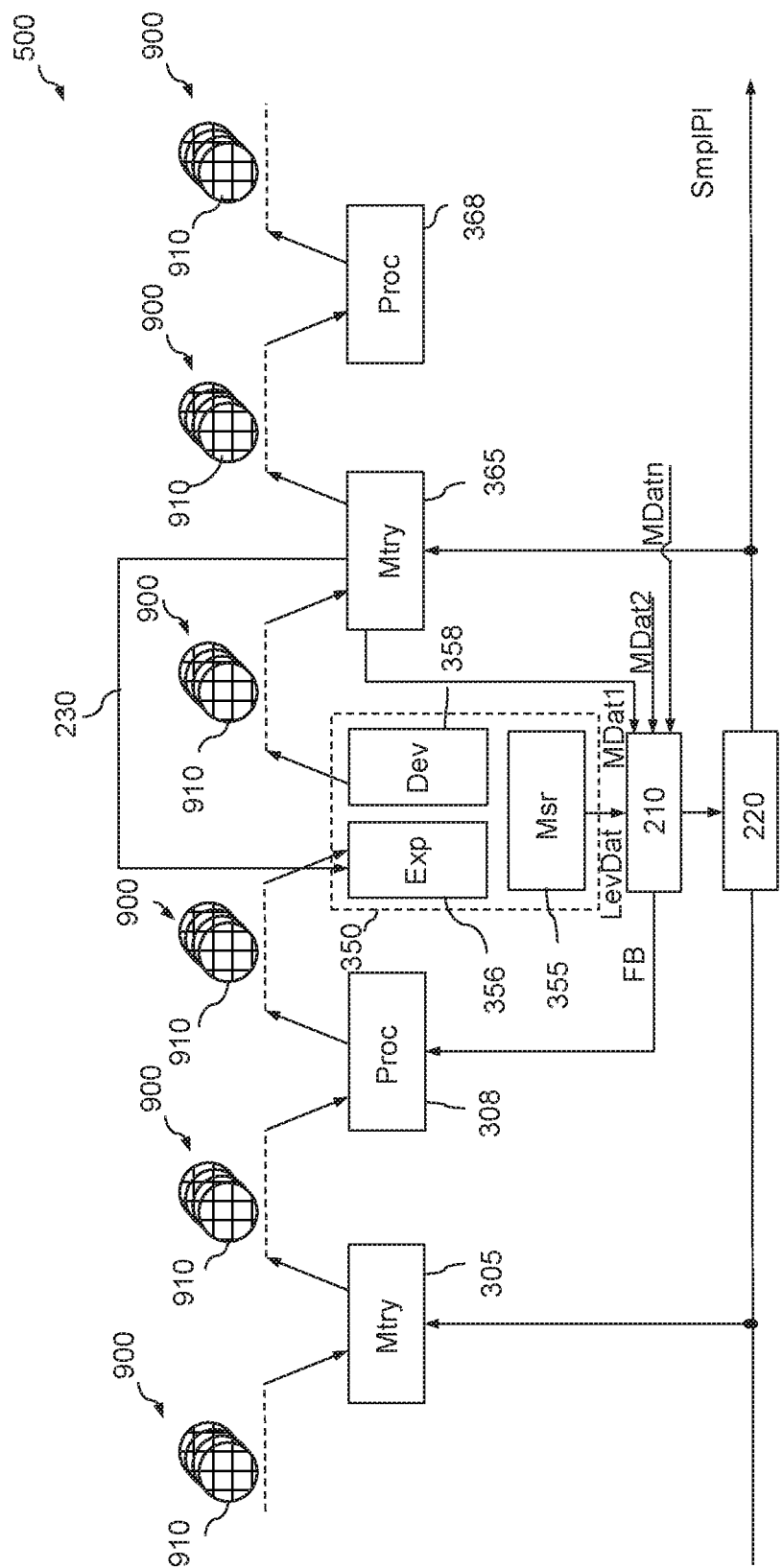
FIG. 7 is a schematic block diagram of a section of a semiconductor manufacturing assembly according to an embodiment using an adaptive wafer model for a feedback loop.

FIG. 7 refers to an embodiment of a section of a semiconductor manufacturing assembly 500 with the high-resolution measurement tool 355 operating in combination with a lithography assembly 350 as illustrated in FIG. 1A. In addition, a feedback path 230 transmits information obtained from the metrology tool 365 back to a control unit of the exposure unit 356 of the lithography assembly 350. The feedback path 230 facilitates compensation of parameter drifts of the exposure unit 356 or the exposure process. By using metrology sites from a sampling plan that more reliably images the parameter drift, the compensation is more effective.

Figure 8A:
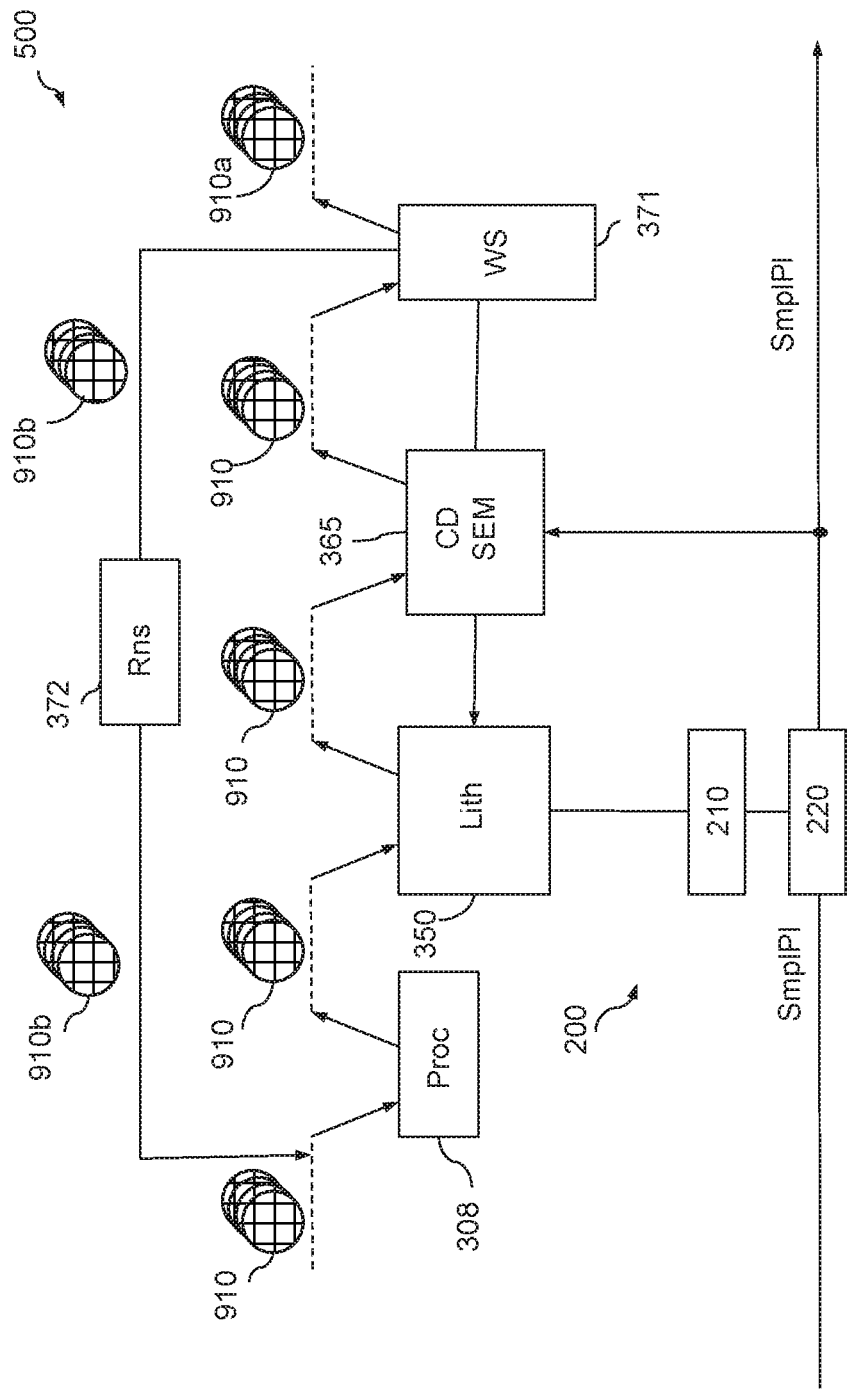
FIG. 8A is a schematic block diagram of a section of a semiconductor manufacturing assembly according to an embodiment using an adaptive wafer model that uses CD (critical dimension) information in addition to levelling data.

In FIG. 8A a semiconductor manufacturing assembly 500 includes an SEM (scanning electron microscope) as metrology tool 365. The SEM may inspect CDs of resist patterns formed on the process wafers 910 in the lithography assembly 350. An output of the SEM may control a wafer selector 371. For example, if the SEM indicates that a developed photoresist structure on a process wafer 910 does not comply with CD specifications, the concerned process wafers 910b may be classified for a rework at the lithography assembly 350. A rework unit 372 may remove the patterned resist from the process wafers 910 classified for rework. Then a new resist layer may be deposited, exposed and developed in the lithography assembly 350. By using metrology sites from a sampling plan that more reliably captures a parameter drift, the rework decision is more reliable and efficient.

Figure 8B:
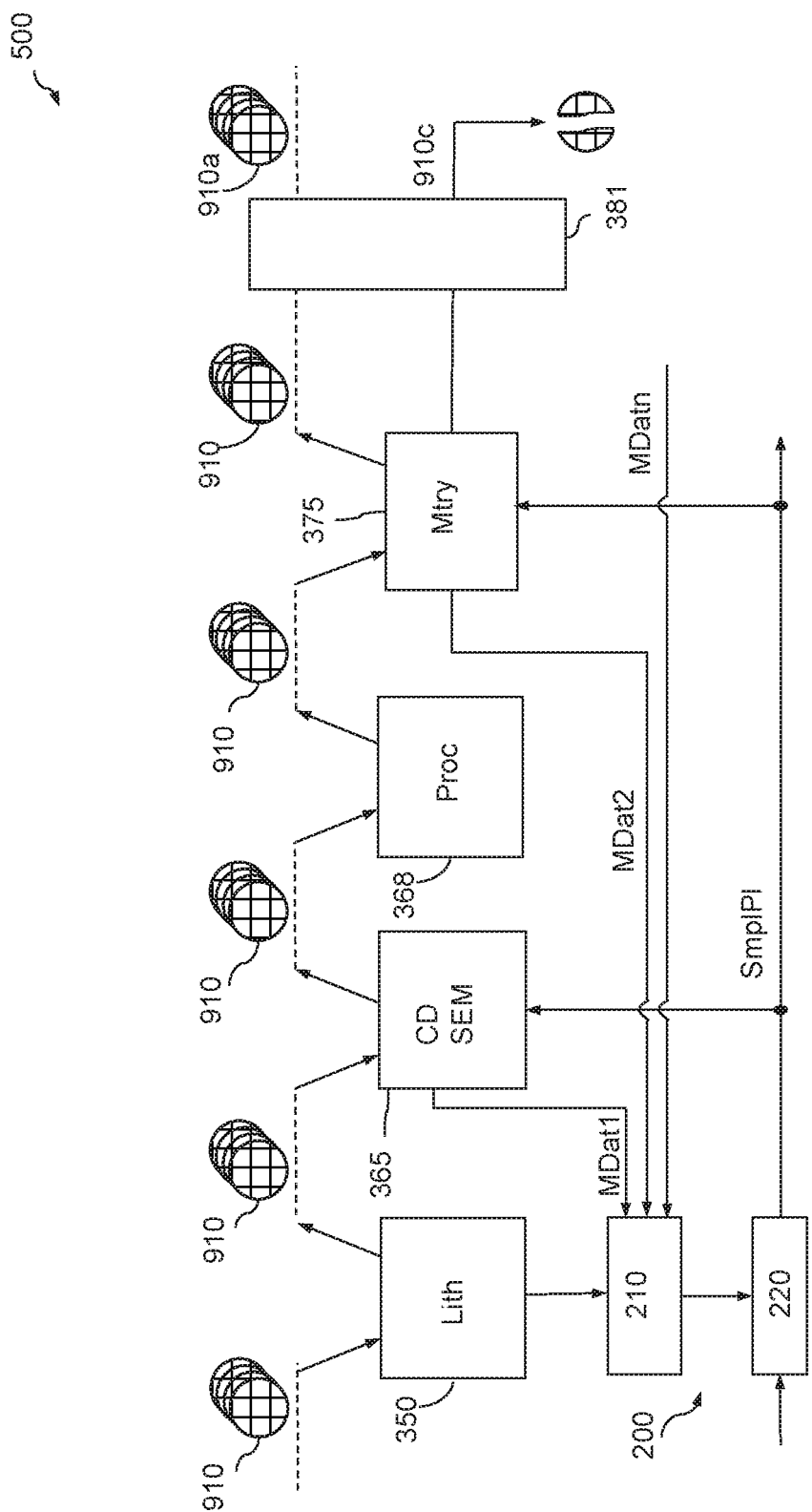
FIG. 8B is a schematic block diagram of a section of a semiconductor manufacturing assembly according to another embodiment.

In FIG. 8B another metrology tool 375 may scan the process wafer 910 for non-reworkable defects. A further wafer selector 381 may discard not-reworkable process wafers 910c. By using metrology sites from a sampling plan that more reliably captures the parameter drift, the decision for discarding or not is more reliable and efficient.

In both cases, process wafers 910a, which comply with the CD tolerances at the metrology sites may be supplied to further processes, wherein critical chip areas or exposure fields may be marked such that semiconductor devices assigned to the critical chip areas or the critical exposure fields can be discarded after the process wafers have been split into a plurality of semiconductor dies. Measurement values of the metrology tool 365 from reliable wafer regions may be fed back to the lithography assembly 350 or may be transmitted to a further control unit for statistical process control or for APC.

What is claimed is:

1. A method of manufacturing semiconductor device, the method comprising:
defining a sampling plan in a process control system, said sampling plan containing position information about metrology sites on process wafers;
measuring a first property of the process wafers with a first metrology tool to obtain measurement values at measurement points and transmitting said measurement values to a process control system, wherein a quantity of the measurement points per process wafer is at least tenfold a quantity of the metrology sites;
updating in said process control system, on the basis of the measurement values, a sampling model that comprises at least a wafer model, wherein the wafer model is based on a model function describing a quantifiable physical property as a function of one or more position variable(s) in closed form;
updating the sampling plan in said process control system on the basis of an assessment of deviations of the measurement values from a current sampling model; and
measuring with a second metrology tool a second property of selected process wafers at metrology sites defined in the sampling plan before updating the sampling plan and measuring with a third metrology tool a third property of the selected process wafers at metrology sites defined in the updated sampling plan.

2. The method of claim 1, wherein the wafer model comprises at least one Zernike polynomial centered to a lateral center point of the wafer model.

3. The method of claim 2, wherein the wafer model comprises at least two Zernike polynomials that comprise dependency on an azimuth angle.

4. The method of claim 2, wherein the wafer model comprises at least Zernike polynomial $Z_1^1$, $Z_1^{-1}$, $Z_2^2$, $Z_4^0$.

5. The method of claim 1, wherein updating the sampling plan comprises replacing metrology sites in wafer regions of the process wafer with large deviations from a wafer model instance with metrology sites with low deviations from the wafer model instance.

6. The method of claim 1, wherein the sampling model comprises a threshold model that contains a position-dependent threshold function and updating the threshold model includes modifying at least one coefficient of the position-dependent threshold function.

7. The method of claim 1, wherein the wafer model contains at least one position-dependent model function and at least one wafer model instance for a collection of process wafers, the wafer model instance defined by a set of coefficients for the wafer model.

8. The method of claim 7, wherein updating the wafer model includes modifying at least one of the coefficients of at least one wafer model instance.

9. The method of claim 7, wherein the collection of process wafers are subjected to equivalent processes at a same process tool before obtaining the measurement values.

10. The method of claim 7, wherein the collection of process wafers is a wafer lot.

11. The method of claim 7, wherein the wafer model includes a wafer model instance covering a complete wafer.

12. The method of claim 7, wherein the wafer model includes a wafer model instance covering an exposure field.

13. The method of claim 1, wherein updating the sampling plan comprises deleting, from the sampling plan, metrology sites in wafer regions of low interest.

14. The method of claim 1, wherein updating the sampling plan comprises adding, to the sampling plan, metrology sites in wafer regions of high interest.

15. The method of claim 1, further comprising:
the measurement values are levelling data representing height maps of the process wafers in a chucked state.

16. The method of claim 1, further comprising:
updating the wafer model on the basis of results of further measurements of the process wafers at the metrology sites.

17. The method of claim 16, wherein the further measurements provide data containing information about wafer bowing and/or wafer warpage.

18. The method of claim 1, further comprising:
modifying the wafer model on the basis of design data.

19. A method of manufacturing a semiconductor device, the method comprising:
defining a sampling plan containing position information about metrology sites on process wafers;
measuring a first property of the process wafers to obtain measurement values at measurement points, wherein a quantity of the measurement points per process wafer is at least tenfold a quantity of the metrology sites;
updating, on the basis of the measurement values, a sampling model that comprises at least a wafer model, wherein the wafer model is based on a model function describing a quantifiable physical property as a function of one or more position variable(s) in closed form; and updating the sampling plan on the basis of an assessment of deviations of the measurement values from a current sampling model, transmitting information contained in the updated wafer model instance to a process tool that is effective on a process wafer before the measurement values are obtained;

changing parameters of a process performed at the process tool in response to the information contained in the updated wafer model instance; and applying the process at the process tool on a further process wafer.

20. A method of manufacturing a semiconductor device, the method comprising:

defining a sampling plan containing position information about metrology sites on process wafers;

measuring a first property of the process wafers to obtain measurement values at measurement points, wherein a quantity of the measurement points per process wafer is at least tenfold a quantity of the metrology sites;

updating, on the basis of the measurement values, a sampling model that comprises at least a wafer model, wherein the wafer model is based on a model function describing a quantifiable physical property as a function of one or more position variable(s) in closed form; and updating the sampling plan on the basis of an assessment of deviations of the measurement values from a current sampling model, transmitting information contained in the updated wafer model instance to a process tool that is effective on a process wafer after the measurement values are obtained and changing parameters of a process performed at the process tool in response to the information contained in the updated wafer model instance; and applying the process at the process tool on a further process wafer.

21. A process control system for a semiconductor manufacturing assembly, the process control system comprising:

a sampling model module adapted to update a sampling model comprising at least a wafer model on the basis of measurement values obtained from a process wafer;

a sampling plan module adapted to update a sampling plan on the basis of an assessment of deviations of the measurement values from the updated sampling model; and a process tool adapted to receive information contained in the updated wafer model instance, wherein the process tool is effective on a process wafer before the measurement values are obtained or is effective on a process wafer after the measurement values are obtained and wherein the process tool is adapted to change parameters of a process performed at the process tool in response to the information contained in the updated wafer model instance.

22. The system of claim 21, wherein the wafer model comprises at least one Zernike polynomial centred to a lateral centre point of the wafer model.

23. The method of claim 22, wherein the wafer model comprises at least two Zernike polynomials that show dependency on an azimuth angle.

* * * * *